US00PP29715P2

(12) United States Plant Patent
Verschoor

(10) Patent No.: US PP29,715 P2
(45) Date of Patent: Sep. 25, 2018

(54) ***ASTILBE* PLANT NAMED 'WHITEBERRY'**

(50) Latin Name: *Astilbe arendsii X Astilbe japonica*
Varietal Denomination: Whiteberry

(71) Applicant: Adrianus Verschoor, Haarlem (NL)

(72) Inventor: Adrianus Verschoor, Haarlem (NL)

( * ) Notice: Subject to any disclaimer, the term of this patent is extended or adjusted under 35 U.S.C. 154(b) by 0 days.

(21) Appl. No.: 15/731,197

(22) Filed: May 1, 2017

(51) Int. Cl.
*A01H 5/02* (2018.01)

(52) U.S. Cl.
USPC ..... Plt./407
CPC ..... *A01H 5/02* (2013.01)

(58) Field of Classification Search
USPC ..... Plt./407
CPC ..... A01H 5/02
See application file for complete search history.

(56) References Cited

FOREIGN PATENT DOCUMENTS

QZ 20170302 4/2017

OTHER PUBLICATIONS

GTITM UPOVROM Plant Variety Database Citation for 'Whiteberry' as per QZ PBR20170302; Apr. 14, 2017; 1 page.*

* cited by examiner

*Primary Examiner* — Kent L Bell
(74) *Attorney, Agent, or Firm* — C. A. Whealy

(57) ABSTRACT

A new and distinct cultivar of *Astilbe* plant named 'Whiteberry', characterized by its compact, broadly upright and mounding plant habit; strong and durable leaves; freely and uniformly flowering habit; white-colored flowers on strong greyed orange-colored peduncles; and good container and garden performance.

2 Drawing Sheets

Botanical designation: *Astilbe arendsii* X *Astilbe japonica.*
Cultivar denomination: 'WHITEBERRY'.

BACKGROUND OF THE INVENTION

The present invention relates to a new and distinct cultivar of *Astilbe*, botanically known as *Astilbe arendsii* X *Astilbe japonica* and hereinafter referred to by the name 'Whiteberry'.

The new *Astilbe* plant is a product of a planned breeding program conducted by the Inventor in Haarlem, The Netherlands. The objective of the breeding program was to create new uniform and freely flowering *Astilbe* plants with attractive leaf and flower coloration.

The new *Astilbe* plant originated from a cross-pollination made by the Inventor in 2010 in Haarlem, The Netherlands, of an unnamed *Astilbe arendsii* seedling selection, not patented, as the female, or seed, parent with an unnamed *Astilbe japonica* seedling selection, not patented, as the male, or pollen, parent. The new *Astilbe* plant was discovered and selected by the Inventor as a single flowering plant from within the progeny of the stated cross-pollination in a controlled greenhouse environment in Haarlem, The Netherlands in 2013.

Asexual reproduction of the new *Astilbe* plant by vegetative divisions in a controlled nursery environment in Heerhugowaard, The Netherlands since the summer of 2013, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Whiteberry'. These characteristics in combination distinguish 'Whiteberry' as a new and distinct *Astilbe* plant:

1. Compact, broadly upright and mounding plant habit.
2. Strong and durable leaves.
3. Freely and uniformly flowering habit.
4. White-colored flowers on strong greyed orange-colored peduncles.
5. Good container and garden performance.

Plants of the new *Astilbe* differ primarily from plants of the parent selections in plant height and flowering habit as plants of the new *Astilbe* are more compact and more freely flowering than plants of the parent selections.

Plants of the new *Astilbe* can be compared to plants of *Astilbe japonica* 'Washington', not patented. In side-by-side comparisons, plants of the new *Astilbe* and 'Washington' differ in the following characteristics:

1. Plants of the new *Astilbe* are more compact than plants of 'Washington'.
2. Plants of the new *Astilbe* have better container performance than plants of 'Washington'.
3. Plants of the new *Astilbe* are more freely flowering than plants of 'Washington'.
4. Plants of the new *Astilbe* and 'Washington' differ in peduncle color as plants of 'Washington' have green-colored peduncles.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Whiteberry' grown in a container.

The photograph on the second sheet is a close-up view of a typical inflorescence of 'Whiteberry'.

DETAILED BOTANICAL DESCRIPTION

The aforementioned photographs and following observations, measurements and values describe plants grown during the summer and early autumn in 21-cm containers in an outdoor nursery in Haarlem, The Netherlands and under cultural practices typical of commercial *Astilbe* production. During the production of the plants, day temperatures ranged from 16° C. to 32° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* X *Astilbe japonica* 'Whiteberry'.

Parentage:

- *Female, or seed, parent*.—Unnamed *Astilbe arendsii* seedling selection, not patented.
- *Male, or pollen, parent*.—Unnamed *Astilbe japonica* seedling selection, not patented.

Propagation:

- *Type*.—By vegetative divisions.
- *Time to initiate roots*.—About three weeks at 20° C.
- *Root description*.—Thick, fleshy; brownish in color.
- *Rooting habit*.—Freely branching; dense.

Plant description:

- *Plant form and growth habit*.—Herbaceous perennial; compact, broadly upright and mounding plant form with inflorescences held above the foliar plane; flowering stems and leaves basal; freely flowering with numerous basal branches developing per plant, dense and bushy; low vigor to moderately vigorous growth habit; and freely and uniformly flowering habit.
- *Growth rate*.—Moderate; from divisions, about 10 months are required to produce fully-grown flowering plants in containers.
- *Plant height* (*soil level to top of foliar plane*).—About 19.6 cm.
- *Plant height* (*soil level to top of inflorescences*).—About 22.3 cm.
- *Plant width* (*spread*).—About 37.3 cm.
- *Stem description*.—Length: About 5.5 cm. Diameter: About 3 mm. Internode length: About 1.3 cm. Strength: Strong. Texture: Sparsely pubescent. Luster: Glossy. Color, developing: Close to 146B tinged with close to 199A. Color, developed: Close to 146C strongly tinged with close to 175B to 175C; at the internodes, close to between 175B and 178A.

Leaf description:

- *Arrangement*.—Alternate; biternately compound; about 17 leaflets per leaf.
- *Leaf length* (*excluding petiole*).—About 14.6 cm.
- *Leaf width*.—About 15.6 cm.
- *Leaflet length*.—About 4.1 cm.
- *Leaflet width*.—About 2.3 cm.
- *Leaflet shape*.—Elliptic.
- *Leaflet apex*.—Abruptly acute.
- *Leaflet base*.—Short attenuate to rounded.
- *Leaflet margin*.—Biserrate.
- *Leaflet texture, upper and lower surfaces*.—Sparsely pubescent.
- *Leaflet luster, upper and lower surfaces*.—Moderately glossy.
- *Leaflet venation pattern*.—Pinnate.
- *Leaflet color*.—Developing leaflets, upper surface: Close to 137A. Developing leaflets, lower surface: Close to between 137B and 146A. Fully expanded leaflets, upper surface: Darker than between 139B and 147A; venation, close to 152A, proximally, close to 183A. Fully expanded leaflets, lower surface: Close to NN137B; venation, close to 148D, proximally, close to 184B.
- *Leaf petiole length*.—About 7.6 cm.
- *Leaf petiole diameter*.—About 2.5 mm.
- *Leaflet petiole length*.—About 6 mm.
- *Leaflet petiole width*.—About 1 mm.
- *Leaf and leaflet petiole texture, upper and lower surfaces*.—Smooth, glabrous.
- *Leaf and leaflet petiole luster, upper and lower surfaces*.—Glossy.
- *Leaf and leaflet petiole color, upper surface*.—Close to 152B tinged with close to 180A.
- *Leaf and leaflet petiole color, lower surface*.—Close to N148A.

Flower description:

- *Flower type and flowering habit*.—Single rotate flowers arranged on terminal compound panicles; flowers face upright, outward or downward depending on position on the inflorescence; panicles roughly conical in shape; freely and uniformly flowering habit with about 1,600 flowers developing per inflorescence.
- *Fragrance*.—Moderately faint; sweet and pleasant.
- *Natural flowering season*.—Plants begin flowering about seven weeks after planting; continuously flowering from late spring throughout the summer in The Netherlands.
- *Postproduction longevity*.—Flowers last about ten days on the plant; flowers persistent.
- *Flower buds*.—Height: About 2 mm. Diameter: About 2 mm. Shape: Globular. Texture: Smooth, glabrous. Luster: Matte. Color: Close to 145B to 145C.
- *Inflorescence height*.—About 17.2 cm.
- *Inflorescence diameter*.—About 9.1 cm.
- *Flower diameter*.—About 7.5 mm.
- *Flower depth*.—About 3.5 mm.
- *Petals*.—Quantity per flower: Typically five in a single whorl. Length: About 3.5 mm. Lobe width: About 0.5 mm. Shape: Oblanceolate. Apex: Acute. Base: Narrowly cuneate. Margin: Entire. Texture, upper and lower surfaces: Smooth, glabrous. Luster, upper and lower surfaces: Matte. Color: Developing petals, upper and lower surfaces: Close to NN155D. Fully expanded petals, upper and lower surfaces: Close to NN155D; color does not change with development.
- *Sepals*.—Quantity per flower: Typically five, occasionally six, in a single whorl, fused towards the base forming a campanulate-shaped calyx. Length: About 2 mm. Width: About 1.5 mm. Shape: Ovate. Apex: Acute. Base: Cuneate, fused. Margin: Entire. Texture, upper and lower surfaces: Smooth, glabrous. Luster, upper and lower surfaces: Matte. Color: Developing sepals, upper and lower surfaces: Close to NN155A; distally, close to 145D. Fully expanded sepals, upper and lower surfaces: Close to 157C; distally, close to 145D.

*Peduncles*.—Length: About 17.2 cm. Diameter: About 3 mm. Angle: Mostly erect. Strength: Strong. Texture: Moderately pubescent. Luster: Moderately glossy. Color: Close to 176A.

*Pedicels*.—Length: About 4 mm. Diameter: About 1 mm. Angle: About 40° from peduncle axis. Strength: Moderately strong. Texture: Sparsely to moderately pubescent. Luster: Matte. Color: Close to 157D.

*Reproductive organs*.—Stamens: Quantity per flower: Typically ten; anthers basifixed. Filament length: About 2 mm. Filament color: Close to NN155A. Anther shape: Broadly ovate. Anther length: About 0.3 mm. Anther diameter: About 0.2 mm. Anther color: Close to 155A. Pollen amount: Scarce. Pollen color: Close to 155D. Pistils: Quantity per flower: Two. Pistil length: About 1.5 mm. Stigma shape: Club-shaped. Stigma color: Close to 150D. Style length: About 1 mm. Style color: Close to 145D. Ovary color: Close to 145C.

*Seeds and fruits*.—Seed and fruit development have not been observed on plants of the new *Astilbe* to date.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Additionally, plants of the new *Astilbe* have been observed to be hardy to USDA Hardiness Zone 5.

It is claimed:

1. A new and distinct *Astilbe* plant named 'Whiteberry' as illustrated and described.

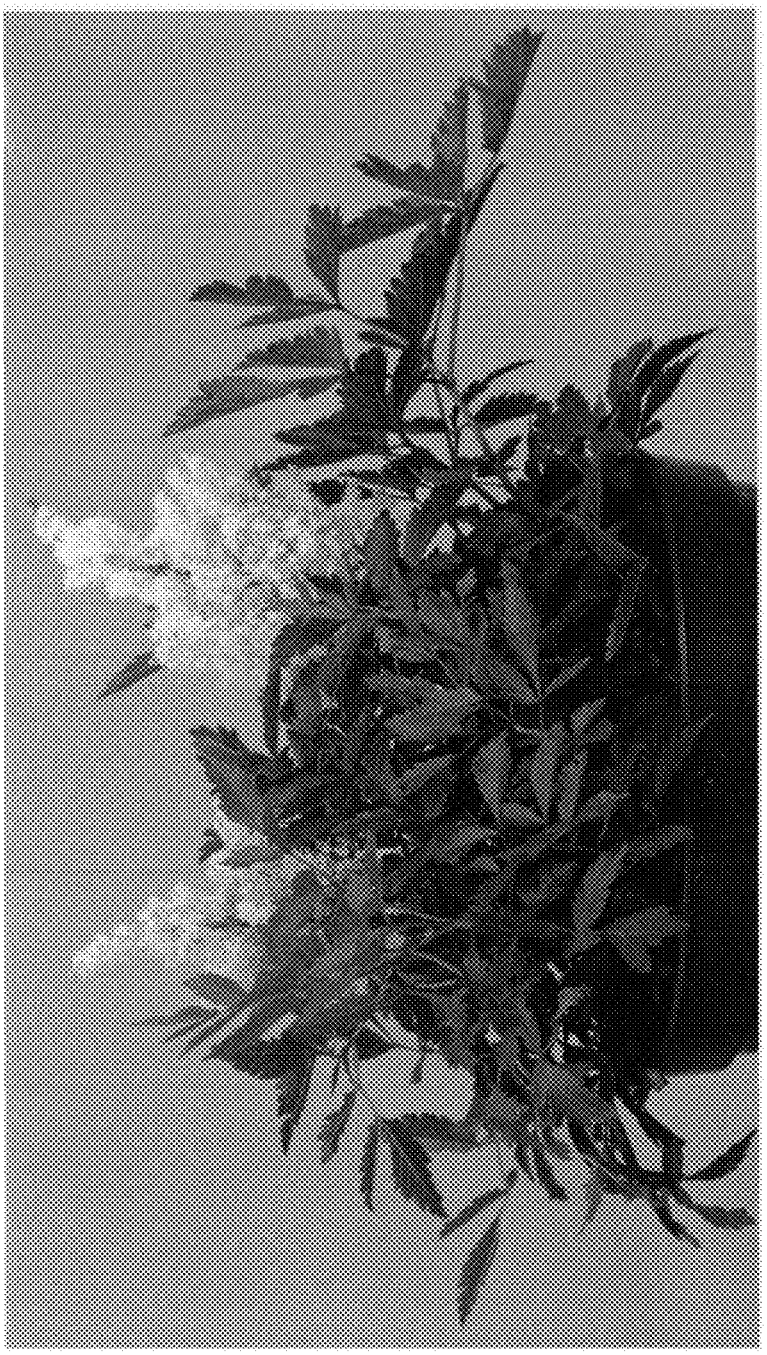

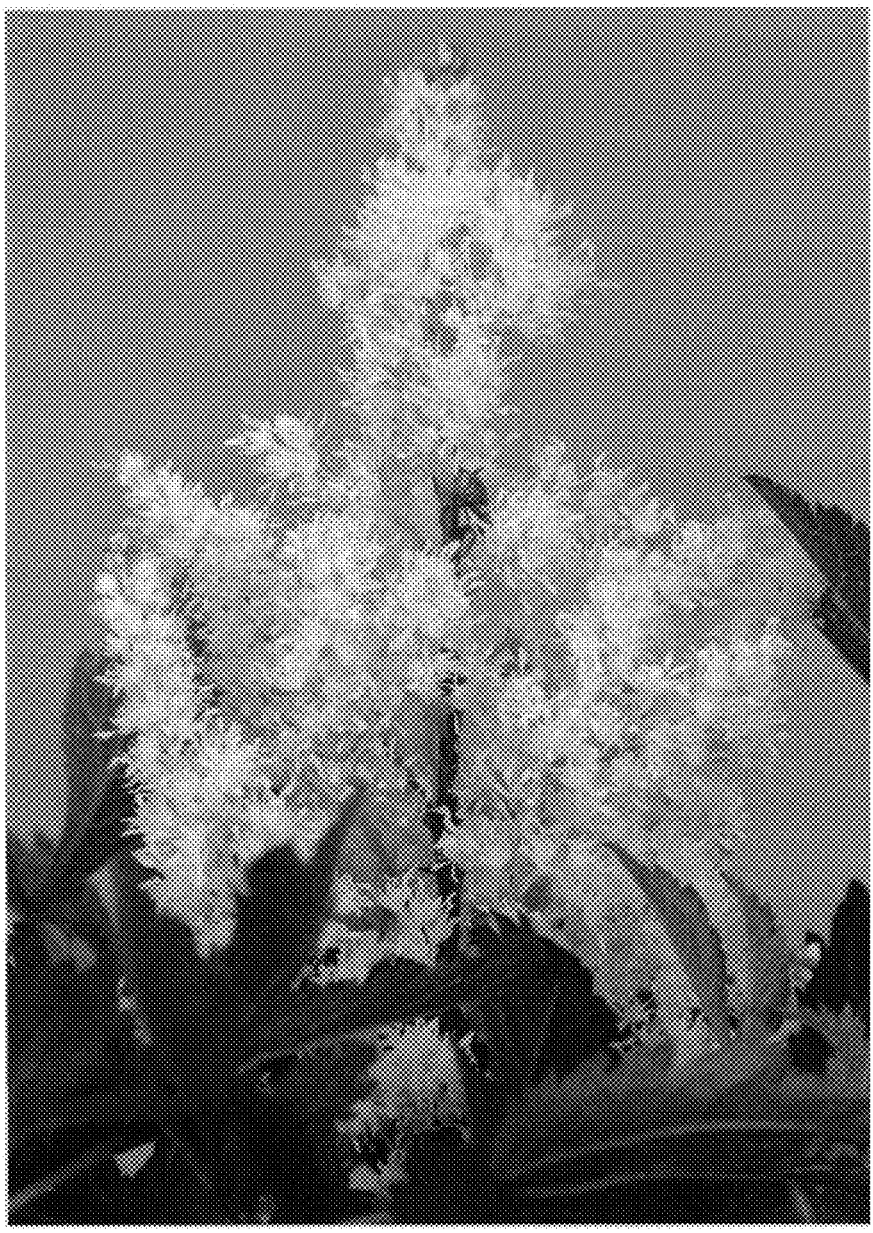

* * * * *